(12) United States Patent
Fitzpatrick

(10) Patent No.: US 7,144,923 B2
(45) Date of Patent: Dec. 5, 2006

(54) METHANOL SYNTHESIS

(75) Inventor: Terence James Fitzpatrick, Cleveland (GB)

(73) Assignee: Johnson Matthey PLC, London (GB)

( * ) Notice: Subject to any disclaimer, the term of this patent is extended or adjusted under 35 U.S.C. 154(b) by 11 days.

(21) Appl. No.: 10/542,819

(22) PCT Filed: Jan. 12, 2004

(86) PCT No.: PCT/GB2004/000075

§ 371 (c)(1),
(2), (4) Date: Jul. 20, 2005

(87) PCT Pub. No.: WO2004/065341

PCT Pub. Date: Aug. 5, 2004

(65) Prior Publication Data

US 2006/0074133 A1    Apr. 6, 2006

(30) Foreign Application Priority Data

Jan. 21, 2003    (GB) ................................ 0301323.2

(51) Int. Cl.
*C07C 27/00* (2006.01)
(52) U.S. Cl. ...................... 518/706; 518/704; 518/705; 518/712

(58) Field of Classification Search ................ 518/706, 518/705, 704, 712
See application file for complete search history.

(56) References Cited

U.S. PATENT DOCUMENTS

| 4,778,662 A | 10/1988 | Pinto |
| 4,788,175 A | 11/1988 | Short et al. |
| 5,252,609 A | 10/1993 | Pinto |
| 5,631,302 A | 5/1997 | König et al. |
| 5,827,901 A | 10/1998 | König et al. |

FOREIGN PATENT DOCUMENTS

| EP | 1 060 788 A1 | 12/2000 |
| EP | 1 080 058 B1 | 12/2003 |
| EP | 1 080 059 B1 | 2/2004 |

*Primary Examiner*—J. Parsa
(74) *Attorney, Agent, or Firm*—RatnerPrestia

(57) ABSTRACT

Methanol is synthesized from pre-heated methanol synthesis gas in one or more adiabatic synthesis stages with cooling of the resultant gas after each stage. Further methanol synthesis is then effected on the resultant partially reacted synthesis gas in a bed of synthesis catalyst cooled by means of a coolant flowing co-currently through tubes disposed in the catalyst bed. After cooling methanol is separated from the unreacted gas. Part of the unreacted gas is combined with make-up gas and used as the coolant fed to the aforesaid tubes, thus producing the pre-heated synthesis gas to be fed to the adiabatic synthesis stages.

6 Claims, 2 Drawing Sheets

METHANOL SYNTHESIS

This application is the U.S. national phase application of PCT International Application No. PCT/GB2004/000075, filed Jan. 12, 2004, and claims priority of British Patent Application No. 0301323.2, filed Jan. 21, 2003.

BACKGROUND OF THE INVENTION

This invention relates to methanol synthesis. Methanol synthesis is generally performed by passing a synthesis gas comprising hydrogen, carbon oxides and any inert gasses at an elevated temperature and pressure through one or more beds of a methanol synthesis catalyst, which is often a copper-containing composition. Methanol is generally recovered by cooling the product gas stream to below the dew point of the methanol and separating off the product as a liquid. The process is often operated in a loop: thus the remaining unreacted gas stream is usually recycled to the synthesis reactor as part of the synthesis gas via a circulator. Fresh synthesis gas, termed make-up gas, is added to the recycled unreacted gas to form the synthesis gas stream. A purge stream is taken from the circulating gas stream to avoid the build up of inert gasses.

It in order to increase the amount of methanol synthesised, it has been proposed in U.S. Pat. Nos. 5,252,609 and 5,631,302 to subject the make-up gas to a preliminary synthesis step before it is added to the synthesis loop. The throughput may also be increased by operating the loop at a lower circulation ratio, which is defined herein as the ratio of the flow rate of the recycled gas to the make-up gas flow rate. Conventionally circulation ratios are about 3.5:1 or higher, but it is desirable to lower the circulation ratio to less than 2.5, e.g. to about 2, in order to minimise the power required for circulation. However, the use of a preliminary synthesis step, or operation at low circulation ratios, has the problem that the partial pressures of the reactants of the gas fed to the preliminary synthesis step, or to the first synthesis stage of the loop, may be relatively high leading to excessive reaction, and excessive heat evolution in the catalyst bed.

Attempts have been made to increase throughput whilst minimising excessive heat generation in the catalyst bed. For example EP 1080058 and EP 1080059 describe multi-stage processes for methanol synthesis. Synthesis is effected in at least two stages in which the first stage reactor may for example be a gas-cooled type as described in U.S. Pat. No. 4,778,662 fed by recycled unreacted gas to which part of the make-up gas has been added, and the second stage being effected on the mixture of the effluent from the first step and the remainder of the make-up gas in a reactor having indirect heat exchange with pressurised water as a coolant. For operation at low circulation ratios, a limitation of this process is the control of temperature in the first stage gas-cooled reactor. When there is a low circulation ratio in the synthesis loop, there may be insufficient cooling gas going through the tubes of the gas-cooled reactor to ensure adequate removal of the reaction heat and so it is difficult to obtain a satisfactory temperature profile through the catalyst bed. High temperatures are detrimental to catalyst life and lead to the formation of by-products, while excessively low temperatures inhibit the desired reaction.

U.S. Pat. No. 5,827,901 describes a methanol synthesis process wherein preheated synthesis gas is reacted in a first reactor wherein the synthesis catalyst is disposed in tubes cooled by heat exchange with water boiling under an elevated pressure. The resultant reacted gas is then fed to a second synthesis reactor wherein further synthesis occurs. The product synthesis gas is then cooled and methanol is separated and the unreacted gas is recycled and fed, together with make-up gas, as the coolant in the second reactor. In this second reactor the coolant removes heat from the reacting synthesis gas, thus heating the coolant, which is then used as the pre-heated synthesis gas fed to the first heat exchange reactor. In the arrangement of U.S. Pat. No. 5,827,901, the gaseous coolant, i.e. the recycled unreacted gas plus make-up gas, flows in a direction counter-current to the flow of the reacting synthesis gas.

SUMMARY OF THE INVENTION

We have devised an alternative arrangement that provides better control of the temperature of the synthesis gas and more efficient heat recovery than the processes described previously.

Accordingly the present invention provides a process for the synthesis of methanol comprising passing a preheated synthesis gas comprising hydrogen and carbon oxides at an elevated pressure through at least one uncooled fixed bed of a methanol synthesis catalyst whereby methanol synthesis is effected adiabatically, cooling the resultant partially reacted synthesis gas by heat exchange with a coolant after passage through each bed, passing the resultant cooled partially reacted synthesis gas through a fixed bed of a methanol synthesis catalyst disposed in a heat exchange reactor having tubes disposed therein through which a coolant is passed in a direction that is co-current with the flow of the partially reacted synthesis gas through the catalyst bed of said heat exchange reactor, whereby further methanol synthesis is effected and the coolant is heated, cooling the resultant reacted synthesis gas to below the dew point of the methanol therein and separating methanol leaving a stream of unreacted gas, passing part of said unreacted gas, together with make-up gas comprising hydrogen and carbon oxides, through said tubes as the coolant of said heat exchange reactor thereby producing the preheated synthesis gas to be fed to said at least one uncooled fixed bed of methanol synthesis catalyst.

Although the fresh synthesis gas, i.e. make-up gas, may be added to the loop at any convenient location, it is preferably added to the recycled synthesis gas before the latter is fed to the tubes as coolant.

Thus in distinction to the arrangement described in the aforesaid U.S. Pat. No. 5,827,901, the synthesis gas used as coolant flows co-currently instead of counter-currently through the heat exchange reactor. Also the reactor cooled by boiling water is replaced by one or more uncooled beds of catalyst in which the synthesis proceeds adiabatically and the heat is recovered as a separate step after at least the first uncooled catalyst bed, and preferably after passage through each uncooled bed except, possibly, the last uncooled bed preceding the bed having the cooling tubes disposed therein. For convenience an uncooled bed will be termed an adiabatic bed and the bed having the coolant tubes extending therethrough will be termed the tube-cooled bed. The partially reacted synthesis gas is preferably not cooled after the last adiabatic bed and before entry into the tube-cooled bed. Thus in a preferred arrangement, the last adiabatic bed before the tube-cooled bed is in effect a "pre-heating" bed sized such that it acts, by virtue of the adiabatic synthesis reaction occurring therein, to heat the synthesis gas from the outlet temperature of the heat recovery step to the desired inlet temperature for the tube-cooled bed. While it is possible to dispose this bed in a separate vessel, in many cases this last adiabatic bed may simply be formed as a layer of catalyst on top of the body of catalyst in the tube-cooled bed. While such a "preheating" bed may be omitted, such omission is less advantageous as the initial part of the tube-cooled bed would have to be employed partly as a region for heating the synthesis gas to the desired maximum synthesis temperature. This would not make the best use of tube-cooled bed. An alternative, or additional, disadvantage of omission of the "pre-heating" bed would be a decrease in the amount of heat recovered prior to the tube-cooled bed. Thus if there was no "pre-heating" bed, and it was desired to make the best use of the tube-cooled bed, then it is necessary that the temperature of the partially reacted gas leaving the heat recovery stage preceding the tube-cooled bed is greater so that the temperature of the partially reacted gas entering the tube-cooled bed is at, or close, to the desired maximum synthesis temperature. Increasing the temperature of the partially reacted gas leaving the heat recovery stage, decreases the temperature differential between the inlet and outlet temperatures of the partially reacted gas undergoing cooling in that heat recovery stage. Decreasing the temperature differential decreases the amount of heat recovered.

Co-current, rather than counter-current, flow of the coolant is advantageous as it enables the tube-cooled bed to operate with a lower peak catalyst temperature (thereby increasing catalyst life and decreasing the amount of by-product formation) and enables the temperature profile in the heat exchange reactor to match more closely the profile corresponding to the maximum rate of methanol synthesis. However one disadvantage of co-current coolant flow is that the temperature of the coolant and product reacted gas leaving the heat exchange reactor is generally too low to recover high grade heat. By subjecting the heated coolant to one or more stages of adiabatic methanol synthesis, followed by heat recovery, higher grade heat can be recovered. The use of adiabatic synthesis catalyst beds plus separate heat recovery is advantageous compared to a system employing a heat exchange reactor using water boiling under pressure as a coolant as it is more flexible. A system using water boiling under pressure is essentially isothermal and the temperature is dictated by the pressure. If the resultant steam is to be used as process steam used to produce the synthesis gas (for example by steam reforming of a hydrocarbon feedstock), the pressure of the reforming operation is thus dictated by the temperature at which the boiling water cooled reactor is to be operated. In contrast, separation of the heat recovery step from the methanol synthesis, by using an adiabatic bed and separate heat recovery, enables higher grade heat to be recovered.

Where the make-up gas is produced by steam reforming, the steam can be introduced by saturation, i.e. by contacting the hydrocarbon feedstock with hot water under a pressure substantially equal to the reforming pressure. However the adiabatic synthesis is not dictated by this pressure.

The methanol synthesis may be performed at pressures in the range 40–150, and more conveniently in the range 45–120, bar abs. The temperature of the synthesis catalyst is suitably in the range 160–300° C.; preferably the peak temperature is below 285° C. The synthesis gas preferably enters the catalyst beds at a temperature in the range 200–250° C. and leaves the beds at temperatures preferably in the range 220–260° C. Such temperatures provide for an acceptable methanol output rate (owing to favourable equilibrium) without producing the greater content of by-product impurities, and reduction in catalyst life, that would result from operation at higher temperatures.

The synthesis catalyst is preferably a copper-based catalyst. Particularly suitable are catalysts containing copper and compounds, e.g. oxides of zinc, aluminium, chromium, titanium, zirconium, and/or magnesium. The catalyst may be in the form of pellets, tablets or extrudates. Particularly preferred catalysts are described in U.S. Pat. No. 4,788,175.

In the process of the invention there are three or more fixed beds of catalyst. One bed is provided with tubes through which synthesis gas is passed as a coolant, while preceding beds are operated adiabatically, i.e. without cooling in the bed. As explained above, after passage through the, or each, adiabatic bed, except, as explained above, preferably the last bed preceding the tube-cooled bed, the reacted gas is cooled by heat exchange with a suitable coolant, which is preferably water under sufficient pressure to prevent boiling. The degree of cooling is such as to bring the temperature of the reacted gas to the desired inlet temperature for the next catalyst bed. It is preferred that the inlet temperature of the second and any succeeding beds is at least 5° C. greater than the inlet temperature of the preceding bed.

In addition to the adiabatic bed, or beds, the process of the invention also employs a bed of catalyst cooled by having heat exchange tubes dispersed therein and through which synthesis gas passes as a coolant in a direction co-current with the flow of synthesis gas through the bed. The catalyst bed may be disposed within a vessel and arranged such that the synthesis gas flows through the bed in a direction parallel to the axis of the vessel (axial flow). The heat exchange tubes may be disposed between a pair of tube sheets dividing the reactor ID into a coolant inlet region, a catalyst-containing region between the tube sheets, and a coolant off-take region. The catalyst-containing region is provided with synthesis gas inlet means to introduce the synthesis gas into the region in the vicinity of the tube sheet between the coolant inlet region and the catalyst-containing region and a reacted synthesis gas outlet means in the vicinity of the tube sheet between the catalyst-containing region and the coolant off-take region. Alternatively the coolant tubes may be disposed between headers. The coolant inlet header is disposed in the vessel in the region adjacent to the catalyst bed inlet while the coolant outlet header is disposed in the region adjacent the catalyst bed inlet. The headers are preferably, but not necessarily disposed, within the catalyst bed. Indeed, as stated above, it may in some cases be desirable to have an uncooled, i.e. adiabatic bed as a layer of catalyst above the inlet to the tube-cooled bed. There may also be an uncooled, i.e. adiabatic, bed immediately following the tube-cooled bed. If used, this should be relatively small compared to the tube-cooled bed and preferably simply comprise catalyst occupying otherwise empty space at the outlet end of the vessel containing the tube-cooled bed.

Alternatively the tube-cooled catalyst bed may be disposed in a reaction vessel as an annular bed with synthesis gas inlet means adjacent the outer periphery of the bed and reacted synthesis gas outlet means adjacent the axis of the vessel, so that the synthesis gas flows radially inwards through the catalyst bed, i.e. in a radial flow reactor. It will be appreciated that by reversing the synthesis gas inlet and outlet means so that the synthesis gas is fed to means adjacent the vessel axis and exits the bed at the periphery thereof, the flow may be radially outwards. In a radial flow arrangement, the coolant tubes will generally be disposed in planes perpendicular to the vessel axis. An example of a suitable radial flow reactor design is shown in EP 1060788.

The tube-cooled catalyst bed and the adiabatic catalyst beds may be disposed in the same vessel or in separate vessels. Multiple adiabatic beds may be disposed in one vessel and the tube-cooled bed, and possibly an adiabatic bed, or beds immediately preceding and/or following the tube-cooled bed, in a separate vessel.

The make-up gas is preferably made by steam reforming a hydrocarbon feedstock, such as methane, natural gas or naphtha, preferably natural gas having a methane content above 90% v/v. In the steam reforming process a mixture of steam and the hydrocarbon feedstock is contacted with a steam reforming catalyst, often nickel on a refractory oxide support, at an elevated pressure, typically in the range 10–50 bar abs., and at an elevated temperature, typically in the range 650–1100° C. The reforming process may be carried out in so-called autothermal reformers or gas-heated reformers. Preferably gas-heated reformers are used wherein the hydrocarbon-steam mixture is first primary reformed by passing it over the reforming catalyst disposed in externally heated tubes, then the primary reformed gas is secondary reformed by partial combustion with an oxygen-containing gas and passing it through a bed of steam reforming catalyst. The secondary reformed gas is used as the heating medium for the primary reforming step.

The mixture of steam and hydrocarbon is preferably produced by contacting the hydrocarbon feedstock with a stream of heated water at a pressure substantially equal to that employed for the reforming step. The stream of heated water is preferably produced by using water as the coolant in the heat exchange means cooling the reacted, and/or partially reacted, synthesis gas.

BRIEF DESCRIPTION OF THE DRAWINGS

The invention is illustrated by reference to the accompanying drawings wherein.

DETAILED DESCRIPTION OF THE INVENTION

Figure 1:
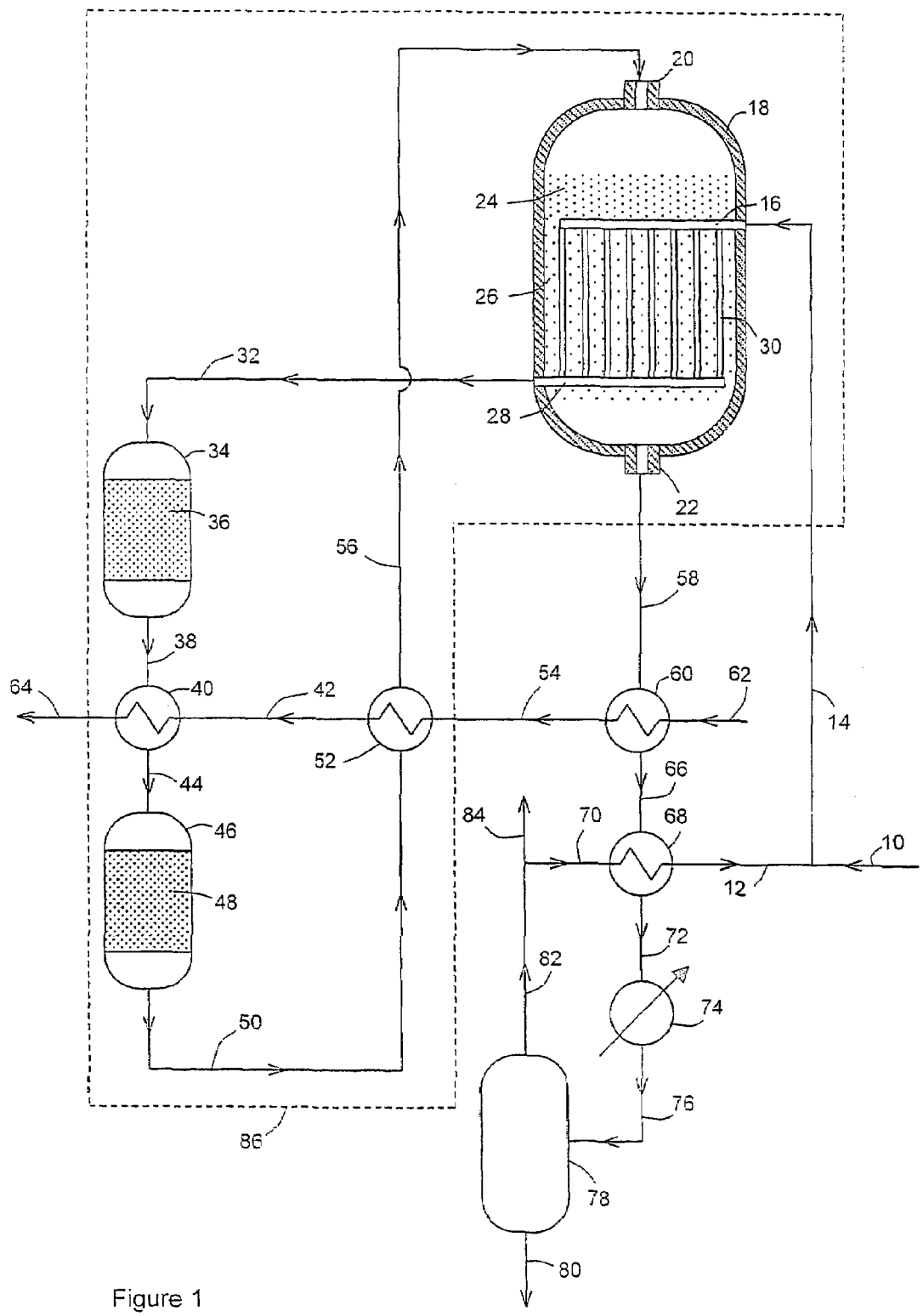
FIG. 1 is a diagrammatic flow sheet of a process in accordance with the invention and FIG. 2 is a graph showing typical temperature profiles in an axial flow reactor having axially extending coolant tubes.

In the embodiment shown in FIG. 1, a methanol synthesis loop is shown. Make-up gas comprising hydrogen, carbon oxides and inert gasses (methane, and possibly nitrogen and argon) is fed via line 10 from a compressor (not shown) and mixed with recycle unreacted gas supplied via line 12. The resulting synthesis gas is then fed via line 14 to the coolant inlet header 16 of a synthesis reactor 18. Reactor 18 is provided with an inlet 20 for partially reacted synthesis gas at one end and an outlet 22 for reacted synthesis gas at the other end with a fixed beds 24, 26 of methanol synthesis catalyst disposed between the inlet 20 and outlet 22. The upper bed 24 is uncooled, while the lower bed 26 is tube cooled. Thus the coolant inlet header 16 is disposed at the inlet end of the bed 26 and a coolant outlet header 28 is disposed towards the outlet end of the bed 26. The bed 26 extends below the coolant outlet header 28 to provide a small un-cooled final portion of the bed 26. A plurality of heat exchange tubes 30 are disposed within the bed connecting the inlet and outlet headers.

The synthesis gas coolant fed to inlet header 16 passes through the tubes 30 absorbing heat from the catalyst bed 26, is combined in outlet header 28 and leaves the reactor 18 as a heated synthesis gas stream via line 32. The heated synthesis gas is then fed via line 32 to the inlet of a vessel 34 containing an uncooled fixed bed 36 of methanol synthesis catalyst. On passage through bed 36, some methanol synthesis occurs adiabatically and the partially reacted synthesis gas leaves vessel 34 via line 38 at a temperature significantly above the temperature at which it entered vessel 34. The partially reacted synthesis gas is then cooled in a heat exchanger 40, typically to a temperature about 5° C. greater than the temperature of the synthesis gas in line 32, by heat exchange with water supplied under pressure to heat exchanger 40 via line 42. The cooled partially reacted synthesis gas is then fed via line 44 to a second vessel 46. Vessel 46 also contains an uncooled fixed bed 48 of methanol synthesis catalyst. During passage through catalyst bed 48, further synthesis occurs with consequent heating of the synthesis gas stream which thus leaves vessel 46 via line 50 at a temperature somewhat greater than the temperature in line 44. The partially reacted synthesis gas in line 50 is then cooled in heat exchanger 52, typically to a temperature about 5° C. greater than the temperature of the synthesis gas in line 44, by heat exchange with water supplied to heat exchanger 52 via line 54. The cooled partially reacted synthesis gas leaves heat exchanger 52 via line 56 and is fed to the inlet 20 of reactor 18.

Further synthesis takes place as the synthesis gas flows through the catalyst beds 24 and 26 in reactor 18. As the synthesis gas passes through the upper bed 24 it partially reacts adiabatically. The heat produced serves to heat the synthesis gas to the desired inlet temperature for bed 26. Further reaction occurs as the synthesis gas passes through bed 26 with heat being absorbed by the coolant synthesis gas flowing through tubes 30. The partially reacted synthesis gas flows through the bed 26 in the same direction as, i.e. co-current with, the flow of synthesis gas as coolant through tubes 30. The reacted synthesis gas leaves reactor 18 via outlet 22 and passes via line 58 to a heat exchanger 60 where it is cooled by water supplied to heat exchanger 60 via line 62.

The water heated in heat exchanger 60 leaves heat exchanger 60 via line 54 and so is further heated in heat exchanger 52. It leaves heat exchanger 52 via line 42 and so is still further heated in heat exchanger 40, giving a stream of hot water in line 64.

The cooled reacted synthesis gas leaves heat exchanger 60 via line 66 and is cooled further in a heat exchanger 68 to which recycled unreacted gas is supplied as a coolant via line 70. The heated recycled unreacted gas leaves heat exchanger 68 via line 12 and so forms part of the synthesis gas fed as coolant to the reactor 18.

The cooled reacted synthesis gas leaves heat exchanger 68 via line 72 and is cooled in one or more stages (indicated by heat exchanger 74) to below the dew point of the methanol in the reacted synthesis gas. The cooled reacted synthesis gas leaves heat exchanger 74 via line 76 and is fed to a separator 78. Crude methanol (containing some water) is separated in separator 78 as product stream 80 while the unreacted gas leaves separator via line 82. Part of the unreacted gas in line 82 is discharged as a purge stream 84 in order to prevent a build up of inert gasses (inerts) in the loop, while the remainder is recycled, via a circulator (not shown), as the recycled unreacted gas stream 70.

If desired the purge gas stream 84 can be passed to a separation unit to recover hydrogen therefrom which is recycled to a convenient location.

It will be appreciated that in some cases the second adiabatic reactor 46 and its associated heat exchanger 52 can be omitted so that the partially reacted synthesis gas leaving heat exchanger 40 is fed directly to the inlet 20 of the tube-cooled reactor 18. Alternatively in other cases it may be desirable to provide for more adiabatic catalyst beds with cooling of the partially reacted synthesis gas between each bed.

In FIG. 1, the synthesis reactors 18, 34 and 46, heat exchangers 40 and 52, and the connecting pipework, are shown within a dotted area 86. For analytical purposes this area can be considered as a "black box". Thus synthesis gas is supplied to the "black box" via line 14 and reacted gas leaves the "black box" via line 58. In addition, partially heated water is fed to the "black box" via line 54 and hot water leaves the "black box" via line 64.

It is readily seen that, if reactors 34 and 46, and heat exchangers 40 and 52, were omitted so that the partially heated synthesis gas from outlet header 28 of reactor 18 was fed directly as the feed synthesis gas to inlet 20 of reactor 18 and any heat losses are ignored, the temperature of the reacted gas leaving vessel 18 via line 58 is determined by the temperature of the feed synthesis gas in line 14, and this temperature is essentially the "control" on the process. The maximum temperature of stream 58 is limited by considerations of the requisite amount of methanol synthesis. Thus for a given feed and operating pressure, the amount of methanol synthesised decreases as the temperature increases. Generally the temperature of stream 58 should be below about 250° C. As a result, while a large amount of heat is available for recovery from the stream 58, the temperature, at which this heat can be recovered, and hence the utility of the recovered heat, is limited.

However, by including the adiabatic reactors 34 and 46 and the cooling by water stream 54, the above limitations are avoided. Thus the system can be more readily controlled since the outlet temperature in line 58 is no longer solely dependent on stream 14 since by controlling the water flow through heat exchangers 52 and 40, the amount of heat removed via stream 64 can be controlled. Also heat is recovered from the reacted gas in line 58 but is upgraded by heat recovered in heat exchangers 52 and 40 where heat can be recovered at higher temperatures since the outlet temperatures from beds 36 and 48 is constrained by catalyst life and by-product considerations rather than the overall amount of methanol production.

Figure 2:
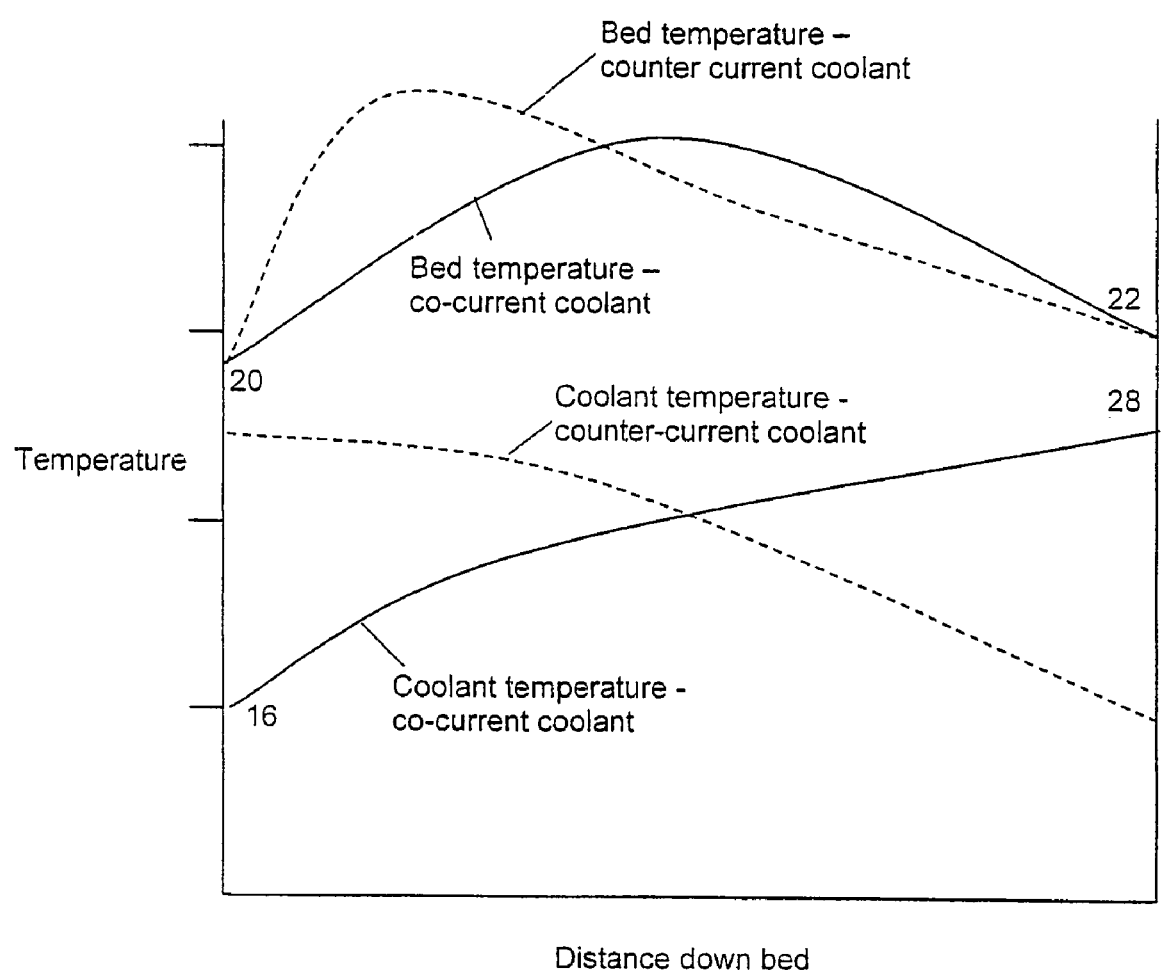

In FIG. 2 there is shown a typical temperature profile through a tube-cooled catalyst bed of the type used in reactor 18 of FIG. 1, but with the adiabatic bed 24, and the adiabatic region of bed 26, below the coolant outlet header 28, omitted. The catalyst bed temperature profile shown as line 20–22 (on the assumption that the synthesis gas enters the bed at the temperature of the partially reacted synthesis gas inlet 20 and leaves the bed at the temperature of the reacted synthesis gas outlet 22) has a peak part way down the bed. Since the coolant is flowing co-currently (line 16–28, i.e. from coolant inlet header 16 to coolant outlet header 28), the temperature difference between the reacting synthesis gas and coolant is large at the inlet end of the bed and small at the outlet end of the bed. This is desirable since the most reaction will occur, and hence the most heat will be produced, in the inlet part of the catalyst bed. As the reacting synthesis gas approached the outlet of the bed, the amount of reaction occurring is much smaller and so the amount of heat that is produced, and to be transferred to the coolant, is smaller and so the amount of cooling required is much smaller. Hence the temperature difference between the reacting gas and coolant is desirably relatively small.

In contrast, in FIG. 2, typical bed and coolant temperature profiles are shown in dotted lines for a tube-cooled bed having counter-current flow coolant where the inlet gas composition and the inlet and outlet bed temperatures are the same as for the co-current coolant case, with the result that the same amount of methanol is synthesised and the same amount of heat is transferred to the coolant. It is seen that the peak temperature is greater. Higher peak temperatures can lead to reduced catalyst performance by sintering of the copper and to increased levels of by-products in the methanol product.

EXAMPLES

The invention is further illustrated by the following calculated examples of a methanol loop designed to produce 2072 tonnes of crude methanol per day. In the tables, the temperatures and flow rates are all rounded to the nearest integer and pressures rounded to the nearest 0.5 bar.

Example 1

In this example the flowsheet is as shown in FIG. 1. The results are shown in Table 1. For convenience of calculation and comparison, the volume of catalyst in bed 26 below the coolant outlet header 28 is assumed to be negligible.

TABLE 1

| stream | Temp (° C.) | Pressure (bar abs.) | Flow rate (kmol/h) | | | | | |
|---|---|---|---|---|---|---|---|---|
| | | | $H_2$ | CO | $CO_2$ | $H_2O$ | inerts | $CH_3OH$ |
| 10 | 130 | 85.0 | 9330 | 1983 | 875 | 38 | 476 | 0 |
| 12 | 177 | 85.0 | 31937 | 500 | 786 | 23 | 4672 | 192 |
| 14 | 165 | 85.0 | 41267 | 2483 | 1661 | 61 | 5148 | 192 |
| 32 | 230 | 84.5 | 41267 | 2483 | 1661 | 61 | 5148 | 192 |
| 38 | 275 | 84.0 | 38817 | 2086 | 1109 | 613 | 5148 | 1141 |
| 44 | 235 | 83.5 | 38817 | 2086 | 1109 | 613 | 5148 | 1141 |
| 50 | 275 | 83.0 | 37433 | 1491 | 1045 | 678 | 5148 | 1801 |
| 56 | 240 | 82.5 | 37433 | 1491 | 1045 | 678 | 5148 | 1801 |
| 58 | 240 | 81.5 | 35051 | 549 | 878 | 844 | 5148 | 2908 |
| 80 | 45 | 80.3 | 10 | 1 | 19 | 818 | 21 | 2698 |
| 82 | 45 | 80.3 | 35041 | 548 | 859 | 26 | 5127 | 211 |
| 84 | 45 | 80.3 | 3103 | 49 | 76 | 2 | 454 | 19 |
| 62 | 200 | 40.0 | 0 | 0 | 0 | 38943 | 0 | 0 |
| 54 | 214 | 39.5 | 0 | 0 | 0 | 38943 | 0 | 0 |
| 42 | 231 | 39.0 | 0 | 0 | 0 | 38943 | 0 | 0 |
| 64 | 250 | 38.5 | 0 | 0 | 0 | 38943 | 0 | 0 |

It is seen that the hot water stream 64 flow rate was 38943 kmol/h and the water temperature was 250° C. The total volume of catalyst required was 116.4 $m^3$, with 24.1 $m^3$ in bed 36, 19.6 $m^3$ in bed 48, 27.7 $m^3$ in bed 24 and 45 $m^3$ in bed 26.

Example 2 (Comparative)

By way of comparison, the Example 1 was changed so that the adiabatic reactors 34 and 46 and heat exchangers 40 and 52 were replaced by a single bed of 50 $m^3$ catalyst cooled by the water stream 54 boiling under pressure passing through tubes extending through the catalyst bed. The results are shown in Table 2.

TABLE 2

| stream | Temp (° C.) | Pressure (bar abs.) | Flow rate (kmol/h) | | | | | |
|---|---|---|---|---|---|---|---|---|
| | | | $H_2$ | CO | $CO_2$ | $H_2O$ | inerts | $CH_3OH$ |
| 10 | 130 | 85.0 | 9330 | 1983 | 875 | 38 | 476 | 0 |
| 12 | 189 | 85.0 | 31949 | 500 | 787 | 23 | 4658 | 192 |

TABLE 2-continued

| stream | Temp (° C.) | Pressure (bar abs.) | Flow rate (kmol/h) | | | | | |
|---|---|---|---|---|---|---|---|---|
| | | | $H_2$ | CO | $CO_2$ | $H_2O$ | inerts | $CH_3OH$ |
| 14 | 174 | 85.0 | 41279 | 2483 | 1662 | 61 | 5134 | 192 |
| 32 | 210 | 84.5 | 41279 | 2483 | 1662 | 61 | 5134 | 192 |
| 56 | 255 | 82.5 | 35873 | 845 | 952 | 771 | 5134 | 2540 |
| 58 | 240 | 81.5 | 35061 | 549 | 879 | 845 | 5134 | 2910 |
| 80 | 45 | 80.3 | 10 | 1 | 19 | 819 | 21 | 2699 |
| 82 | 45 | 80.3 | 35051 | 548 | 859 | 26 | 5113 | 211 |
| 84 | 45 | 80.3 | 3103 | 49 | 76 | 2 | 454 | 19 |
| 62 | 110 | 40.5 | 0 | 0 | 0 | 3947 | 0 | 0 |
| 54 | 220 | 40.0 | 0 | 0 | 0 | 3947 | 0 | 0 |
| 64 | 252 | 40.0 | 0 | 0 | 0 | 3947 | 0 | 0 |

It is seen that the hot water stream 64 flow rate was 3947 kmol/h and the water temperature was 252° C. The total volume of catalyst required is thus 122.7 m³, i.e. over 5% more than in Example 1.

Example 3 (Comparative)

By way of comparison, the arrangement of Example 1 was changed by reversing the coolant inlet and outlet to the tube-cooled reactor 13 so that the coolant flow through the tubes of reactor 18 was counter-current, then in order to obtain the same amount of product, the flow rates and temperatures are re-calculated as shown in the following Table 3a.

TABLE 3a

| stream | Temp (° C.) | Pressure (bar abs.) | Flow rate (kmol/h) | | | | | |
|---|---|---|---|---|---|---|---|---|
| | | | $H_2$ | CO | $CO_2$ | $H_2O$ | inerts | $CH_3OH$ |
| 10 | 130 | 85.0 | 9330 | 1983 | 875 | 38 | 476 | 0 |
| 12 | 176 | 85.0 | 31953 | 490 | 769 | 23 | 4681 | 192 |
| 14 | 165 | 85.0 | 41284 | 2473 | 1664 | 61 | 5157 | 192 |
| 32 | 230 | 84.5 | 41284 | 2473 | 1664 | 61 | 5157 | 192 |
| 38 | 275 | 84.0 | 38843 | 2075 | 1096 | 610 | 5157 | 1138 |
| 44 | 235 | 83.5 | 38843 | 2075 | 1096 | 610 | 5157 | 1138 |
| 50 | 275 | 83.0 | 37459 | 1480 | 1032 | 674 | 5157 | 1798 |
| 56 | 240 | 82.5 | 37459 | 1480 | 1032 | 674 | 5157 | 1798 |
| 58 | 240 | 81.5 | 35062 | 538 | 861 | 845 | 5157 | 2911 |
| 0 | 45 | 80.3 | 10 | 1 | 19 | 819 | 21 | 2701 |
| 82 | 45 | 80.3 | 35052 | 537 | 842 | 26 | 5137 | 211 |
| 84 | 45 | 80.3 | 3098 | 47 | 74 | 2 | 454 | 19 |
| 62 | 200 | 40.0 | 0 | 0 | 0 | 38914 | 0 | 0 |
| 54 | 214 | 39.5 | 0 | 0 | 0 | 38914 | 0 | 0 |
| 42 | 231 | 39.0 | 0 | 0 | 0 | 38914 | 0 | 0 |
| 64 | 250 | 38.5 | 0 | 0 | 0 | 38914 | 0 | 0 |

The catalyst volumes required for beds 36 and 48 were the same as in Example 1, namely 24.1 m³ and 19.6 m³ respectively. The volume of catalyst required in adiabatic bed 24 was 27.9 m³, i.e. fractionally more than in Example 1. However the volume required in bed 26 was 60 m³, thus giving a total catalyst volume of 131.4 m³, i.e. almost 13% more than in Example 1. Calculated temperature profiles, for bed 26, were as set out in the following Table 3b. The temperatures quoted are the outlet boundary (reactants or coolant as the case may be) for each volume increment of the bed.

TABLE 3b

| Catalyst volume from top of bed 26 (m³) | Example 1 - co-current temperature (° C.) | | Example 3 - counter-current temperature (° C.) | |
|---|---|---|---|---|
| | Reactants | Coolant | Reactants | Coolant |
| 0 | 275 - (inlet) | 165 (inlet) | 275 (inlet) | 229 (outlet) |
| 9 | 251 | 197 | | |
| 12 | | | 270 | 219 |
| 18 | 242 | 213 | | |
| 24 | | | 264 | 208 |
| 27 | 239 | 222 | | |
| 36 | 239 | 228 | 258 | 195 |
| 45 | 240 (outlet) | 230 (outlet) | | |
| 48 | | | 250 | 181 |
| 60 | | | 240 (outlet) | 165 |

Example 4 (Comparative)

By way of comparison, Example 1 is modified by omitting the reactors 34 and 46 and heat exchangers 40 and 52 so that the heated coolant leaving the coolant outlet header 28 is fed directly to the inlet 20 of reactor 18. The results are shown in Table 4.

TABLE 4

| stream | Temp (° C.) | Pressure (bar abs.) | Flow rate (kmol/h) | | | | | |
|---|---|---|---|---|---|---|---|---|
| | | | $H_2$ | CO | $CO_2$ | $H_2O$ | inerts | $CH_3OH$ |
| 10 | 130 | 85.0 | 9330 | 1983 | 875 | 38 | 476 | 0 |
| 12 | 76 | 85.0 | 31939 | 502 | 788 | 23 | 4665 | 192 |
| 14 | 89 | 85.0 | 41270 | 2485 | 1663 | 61 | 5141 | 192 |
| 32 | 230 | 84.5 | 41270 | 2485 | 1663 | 61 | 5141 | 192 |
| 58 | 240 | 81.5 | 35049 | 549 | 880 | 845 | 5141 | 2911 |
| 80 | 45 | 80.3 | 10 | 1 | 19 | 819 | 21 | 2700 |
| 82 | 45 | 80.3 | 35039 | 548 | 860 | 26 | 5121 | 211 |
| 84 | 45 | 80.3 | 3103 | 49 | 76 | 2 | 454 | 19 |
| 62 | 200 | 40.0 | 0 | 0 | 0 | 37098 | 0 | 0 |
| 54 | 215 | 39.5 | 0 | 0 | 0 | 37098 | 0 | 0 |

The volume of catalyst required in beds 24 and 26 is 24.1 m³ and 115 m³, i.e. a total of 139.1 m³. This is about 19.5% more than the Example of the invention, Example 1. It is seen that the hot water produced from heat recovery from the reacted synthesis gas had a temperature of only 215° C., whereas the Example 1 produced almost 5% more hot water at a temperature of 250° C., i.e. 35° C. higher. Hence clearly not only is there a significant catalyst saving as a result of the invention, but also more higher grade heat is recoverable. This example also shows that if there is no cooling of the heated coolant leaving outlet header 28 then the bed 26 cooling in heat exchange reactor 18 has to be effected by employing very low inlet (or recycle) gas temperature.

The invention claimed is:

1. A process for the synthesis of methanol, comprising the steps of:
  passing a preheated synthesis gas comprising hydrogen and carbon oxides at an elevated pressure through at least one uncooled fixed bed of a methanol synthesis catalyst wherein methanol synthesis is effected adiabatically,
  cooling the resultant partially reacted synthesis gas by heat exchange with a coolant after passage through each bed, passing the resultant cooled partially reacted synthesis gas through a fixed bed of a methanol synthesis catalyst disposed in a heat exchange reactor having tubes disposed therein through which a coolant is passed in a direction that is co-current with the flow of the partially reacted synthesis gas through the catalyst bed of said heat exchange reactor whereby further methanol synthesis is effected and the coolant is heated, cooling the resultant reacted synthesis gas to below the dew point of the methanol therein and separating methanol leaving a stream of unreacted gas, passing part of said unreacted gas, together with make-up gas comprising hydrogen and carbon oxides, through said tubes as the coolant of said heat exchange reactor thereby producing the preheated synthesis gas to be fed to said at least one uncooled fixed bed of methanol synthesis catalyst.

2. The process according to claim 1, wherein, prior to passage through the fixed bed of methanol synthesis catalyst cooled by coolant passing through tubes disposed in the heat exchange reactor, the cooled partially reacted synthesis gas is passed through an uncooled fixed bed of a methanol synthesis catalyst wherein methanol synthesis is effected adiabatically, without subsequent cooling of the resultant synthesis gas.

3. The process according to claim 1, wherein the preheated methanol synthesis gas is subjected to two stages of adiabatic methanol synthesis with cooling of the partially reacted synthesis gas after each stage.

4. The process according to claim 1, wherein the temperature at which the synthesis gas enters the second and any succeeding beds is at least 5° C. greater than the temperature at which it entered the preceding bed.

5. The process according to claim 1, wherein the coolant used to cool the partially reacted synthesis gas after the, or each, stage of adiabatic methanol synthesis is water under sufficient pressure to prevent boiling.

6. The process according to claim 5, wherein the make-up gas is produced by a process including a step of steam reforming wherein a mixture of steam and a hydrocarbon feedstock is contacted with a steam reforming catalyst at an elevated pressure, and temperature, and said mixture of steam and hydrocarbon feedstock is produced by contacting the hydrocarbon feedstock with the heated water formed as a result of the use of water as the coolant.

* * * * *